United States Patent [19]

Reichenberger

[11] 4,016,869
[45] Apr. 12, 1977

[54] SIGNAL COLLECTOR SYSTEM

[75] Inventor: Helmut Reichenberger, Brand, Germany

[73] Assignee: Siemens Aktiengesellschaft, Berlin & Munich, Germany

[22] Filed: Oct. 30, 1975

[21] Appl. No.: 627,465

[30] Foreign Application Priority Data

Nov. 18, 1974 Germany .......................... 2454567

[52] U.S. Cl. ...................... 128/2.1 E; 128/DIG. 4; 252/518
[51] Int. Cl.² .......................................... A61B 5/04
[58] Field of Search .......... 128/2.06 E, 2.1 E, 404, 128/410, 411, 416–418, DIG. 4; 252/518

[56] References Cited

UNITED STATES PATENTS

| 3,027,333 | 3/1962 | Friedman | 128/417 A |
|---|---|---|---|
| 3,048,549 | 8/1962 | Adams | 128/417 A |
| 3,151,619 | 10/1964 | Sullivan | 128/417 |
| 3,387,608 | 6/1968 | Figar | 128/2.06 E |
| 3,496,929 | 2/1970 | Domingues | 128/2.06 E |
| 3,518,984 | 7/1970 | Mason | 128/2.06 E |
| 3,528,408 | 9/1970 | Opperman | 128/2.1 E |
| 3,547,104 | 12/1970 | Buffington | 128/2.06 E |
| 3,567,657 | 3/1971 | Lichtenstein | 128/417 A |
| 3,911,906 | 10/1975 | Reinhold, Jr. | 128/2.06 E |

*Primary Examiner*—Robert W. Michell
*Assistant Examiner*—Lee S. Cohen
*Attorney, Agent, or Firm*—Hill, Gross, Simpson, Van Santen, Steadman, Chiara & Simpson

[57] ABSTRACT

A signal collector system, in particular for electrical body signals, consisting of at least one electrode and a contact paste which is to be introduced, at the applicating location, intermediate the body and the electrode. The electrode provides for the extensive avoidance of the effect of the forces and twisting moments which attack it in its applied condition by forming on the body a homogeneous contact paste and adhesive with a conductive substance having a salve or syrup like consistency for the electrode.

6 Claims, 2 Drawing Figures

SIGNAL COLLECTOR SYSTEM

FIELD OF THE INVENTION

The present invention relates to signal collector system, in particular for electrical body signals, consisting of at least one electrode and a contact paste which is to be introduced, at the applicating location, intermediate the body and the electrode.

An undisturbed signal take-off or collection by means of electrodes from a body is preconditioned on that the electrodes are in continual good contact with the body during the measuring period, meaning, that even during relatively strong body movements they will not loosen at the applicating location or, respectively, fall off from the body.

DISCUSSION OF THE PRIOR ART

For example, a sufficiently good degree of adhesion is achieved when the electrode is glued or pasted on at the applicating location. Among others, an electrode of that type is known which is adapted to be pasted onto the patient's body by means of a crossed-over adhesive foil. For the protection of the adhesive surface of the adhesive foil there serve two protective papers which are superimposed thereon, which are pulled off from the foil only immediately prior to the application of the electrode. Preceding the application of the electrode, a contact paste or, respectively, a contact gelatin, is additionally introduced intermediate the body and the electrode, which is adapted to improve the conductivity between the electrode and the skin.

Furthermore, there is presently known a contact layer for electrodes which is constituted of an absorbent material and which contains salts in a dry condition which, in combination with water, produce an electrolytic fluid. Such a layer becomes electrically conductive through moistening with water, and thereby ready for use. For the pasting on of the electrode including the layer onto the patient's body, there serves a special adhesive means, for example, dextrin which, upon occasion, can be contained already in a dry condition within the actual contact layer.

The first mentioned adhesive electrode is quite difficult in the handling thereof inasmuch as, preceding the application thereof, the protective paper must first be removed in a time consuming manner. Smudging of the contact paste during application can additionally adversely influence the adhesiveness of the adhesive foil. Moreover, the removal of the electrode from the body is not carried out completely without pain since, during the tearing off of the adhesive foil, there may be torn off therewith, for example, adherent or pasted on hairs. During the frequent repositioning of the electrodes on the patient's body, this leads to a not inconsiderable annoyance of the patient.

The second adhesive electrode is subject to similar disadvantages. Although, prior to application, no protective layers need be drawn off from the adhesive surface of the adhesive foil, for this purpose the contact layer, however, requires a pretreatment with water which, similarly, is time consuming and, in addition, may influence the adhesiveness of the adhesive means. The tearing off of this electrode similarly may be painful as with respect to the above described adhesive electrode. Moreover, the complex construction of the contact layer inherently will carry along increased production costs, which will raise the overall costs of the signal collection system in an undesirable measure.

SUMMARY OF THE INVENTION

Accordingly, it is an object of the present invention to provide a signal take-off or collection system of the above-mentioned type which, in its entirety, will not incorporate the disadvantages encountered in the above-described systems.

The foregoing object is inventively attained in that the electrode is provided with means for the extensive avoidance of the effect of the forces and twisting moments which attack it in its applied condition, and which forms on the body a homogeneous contact paste and adhesive means with a conductive substance having a salve-or syrup-like consistency for the electrode.

Force resistant electrodes which are particularly well balanced, as has been shown through practical experimentation, facilitate in conjunction with contact pastes pursuant to the invention a sufficiently good adherence to the patient's body over also longer time periods, without the heretofore required auxiliary measures of application aides, for example, additional adhesive means or the like. The application process hereby is not only rendered easier in the sense that the electrodes can be applied more rapidly to the patient's body than heretofore, but also may again be removed from the patient's body with less pain; at an extensively disturbance resistant signal take-off, the system components are now limited to essentially only two components, meaning, the electrodes and the paste, which are separate prior to the application. This not only affords manufacturing simplifications, but now also provides the advantage of a cost-saving multiple use for the electrodes, since the electrodes which are freed from pastes or adhesive components can be easily sterilized without problems prior to their use. The electrode systems in the current state of the art do not permit any renewed sterilization, and are there merely destined for disposal after single use.

In a preferred embodiment of the invention, there may be employed light electrodes having low centers of gravity and a connector cable conducted essentially in parallel with the surface of the electrode, which are modified in a manner wherein the electrode on the side thereof which is diametrically opposite to the cable end point is provided with a balancing weight balance which essentially cancels out the torques caused by the weight of the cable. For the producing of a weight balance, the electrode may hereby be formed more massive at the side diametrically opposite the cable end point than at the side of the cable end point. Preferably, the balancing weight should, however, be at least partly formed by means of a connector portion for the connector cable which, in a weightwise loading manner, affects the side of the electrode which is diametrically opposite to the cable end point. When the connector portion is formed as a socket connector for a plug connection, for example, a banana or split plug provided on the connector cable, then the socket connector suitably should be a metal tube preferably extending from the electrode edge in a direction towards the middle of the electrode which, in the region of the electrode middle, evidences plug-in aperture for the plug connection of the connector cable. As the cable end point there is hereby to be understood any point at the edge of the electrode surface at which the connector cable is conducted away from the electrode.

To be taken into consideration for use as contact pastes are, for example, vaseline or dextrin or, respectively, tylose pastes which are enriched with conductive substances. Preferably, however, should be employed a contact paste which evidences polyethylene glycol (PEG) as the base material. The indicated pastes evidence a viscosity which, on the one hand, is sufficiently low for an easy applicability to the electrode and skin sufficiently and, on the other hand, is sufficiently high for affording a good adherence between the electrode and skin. Furthermore, they have a good skin capatibility meaning, they are not toxic; can take the temperature variations between 20° and 45° C without influencing their function, and are storable for adequately lengthy periods without the occurrence of variations in consistency due to drying out, unmixing, or the like, or spoilage, for example, due to the presence of microorganisms or the like. In connection with the added conductive substances such as, for example, an aqueous NaCL solution, these pastes further achieve a high degree of conductivity, as well as a sufficient depolarizing effect with regard to the electrode reactions, meaning, among other factors, a rapid adjustment to a stable potential.

Particularly good conditions in the above-mentioned context are achieved by means of contact pastes in which there are utilized, as the base material, mixtures which are fluid at body temperature and relatively solid (wax-like) polyethylene glycols, for example, such having molecular weights of about 400 and such of about 6000. Preferably hereby there should be employed base mixtures which, relative to the entire paste, are constituted of about 50 percent from PEG 200 and about 35 percent from PEG 6000, or one portion from PEG 300 as well as a further portion from PEG 600 and from two portions of PEG 4000, whereby the PEG-base mixture has admixed therewith, preferably, a further 10 percent aqueous NaCL-solution as the conductive substance, as well as 5 percent cetylalcohol as an emulsifier. The NaCL solution hereby should additionally contain 0.1 m NaK/tartrate as a depolarizer.

BRIEF DESCRIPTION OF THE DRAWINGS

Further advantages and details of the invention may now be ascertained from the following description thereof, taken in conjunction with the accompanying drawings; in which.

DETAILED DESCRIPTION

Figure 2:
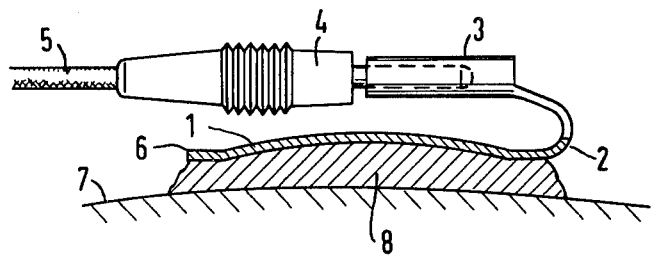
FIG. 2 illustrates the signal collector system of FIG. 1 in a side view, shown partly in section.
Figure 1:
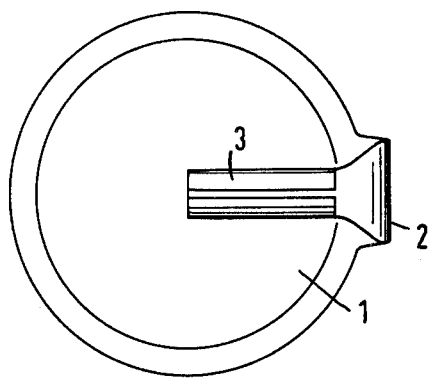
FIG. 1 illustrates a plan view of a signal collector system constructed pursuant to the invention.

In FIGS. 1 and 2, a thin high-grade or stainless steel electrode preferably constituted of NiMo-steel, is designated by reference numeral 1, which is slightly concavely curved on the application side thereof. Conductively connected to the electrode at a side edge of the electrode 1, at a point 2, is a socket connector 3 for the plug connector 4 (2 mm-banana plug) of a signal cable 5. The socket connector 3 is formed as a slotted metallic tube which evidences a length corresponding to about one-half of the diameter of the electrode surface. The arrangement of the tube 3 across the electrode surface is so arranged whereby the plug-in aperture of the tube for the plug connector 4 of the signal cable 5 is located about in the middle of the electrode. The cable which is connected thereto hereby evidences a cable end point 6 which is diametrically opposite to the connecting point 2 of the socket connector 3 on the electrode surface.

The weight of the tube is selected approximately in conformance with the cable connector weight. With a connected cable 4, 5, the center of gravity of the entire system of the cable plug connector and the metal tube, in addition to the electrode, is essentially located in the axis of symmetry of the electrode. The forces or torques which act on the applied electrode are thereby extensively cancelled or compensated for due to the symmetrical weight distribution, and can also no longer be the cause for any undesired positional changes of the electrode.

For adhering or pasting the electrode to the skin 7 of a patient, there serves a contact paste 8 which preferably consists of 50 percent PEG 200, 35 percent PEG 6000, a 10 percent aqueous solution with 5 m NaCl as the conductive substance, and 0.1 m NaK-tartrate as a depolarizer, as well as 5 percent cetyl alcohol as an emulsifier.

The exemplary embodiment may be varied as desired within the scope of the invention and disclosure. In addition to the utilization of otherwise constructed contact paste mixtures, for instance, such as in the previously described art, for example, the electrode may also be extensively modified so that the socket plug tube 3 for the cable connector 4 is not applied with a soldering plug, but directly welded or glued onto the electrode plate 1. In lieu of the plug connectors, spring clip connectors or the like may also find use. The electrode may further be insulated by means of a plastic material on the electrode surface which is opposite to the application surface, so that, for example, the cable connector conduit can also be sprayed into the plastic material. The cable connection may be traction relieved and, as a weight balance, the plastic material or the electrode material may be more massive on the side of the electrode diametrically opposite the cable end point than on the side of the cable end point. Applicable as the electrode materials there may further be utilized, in addition to NiMo-steel, also such suitable metals or alloys as, for instance, quicksilver, silver, rhodium, Ag/AgCL, as well as conductive plastic materials and elastomers, for example, based on epoxy resins, silicon rubber, respectively, also graphite. All of these possible variations fall within the scope of the invention.

While there has been shown what is considered to be the preferred embodiment of the invention, it will be obvious that modifications may be made which come within the scope of the disclosure of the specification.

What is claimed is:

1. In a signal collector system, particularly for electrical body signals and the like, including at least one electrode connectable to a signal cable; and an electrically conductive paste positioned on said electrode at an application location, said electrode comprising means for extensively eliminating effects of forces and torques acting on said electrode in the applying position thereof, said paste forming a contact paste and adhesive for the electrode on said body, the improvement comprising: said contact paste comprising polyethylene glycol (PEG) as the base material thereof, said base material comprising mixtures of polyethylene glycol with at least one portion being fluid at body temperature and another portion being relatively solid at body temperature, said one portion of said mixture having a molecular weight of about 400 and said another portion having a molecular weight of about 6000.

2. A system as claimed in claim 1, said base mixture, relative to the entire paste, being about 50 percent of PEG 200 and about 35 percent of PEG 6000.

3. A system as claimed in claim 1, said base mixture, relative to the entire paste, having one part of PEG 300, a second part of PEG 600, and two parts of PEG 4000.

4. A system as claimed in claim 1, said PEG base mixture including an admixture of a conductive substance constituted of a 10 percent aqueous NaCl solution.

5. A system as claimed in claim 4, said solution comprising 5 m NaCl and containing 0.1 m NaK-tartrate as a depolarizer.

6. A system as claimed in claim 5, said base mixture including an emulsifier of 5 percent cetyl alcohol.

* * * * *